United States Patent
He

(10) Patent No.: US 11,373,299 B2
(45) Date of Patent: Jun. 28, 2022

(54) X-RAY EXPOSURE AREA REGULATION METHOD, A STORAGE MEDIUM, AND AN X-RAY SYSTEM

(71) Applicant: Siemens Healthcare GmbH, Erlangen (DE)

(72) Inventor: Wei He, Shanghai (CN)

(73) Assignee: Siemens Heathcare GmbH, Erlangen (DE)

( * ) Notice: Subject to any disclaimer, the term of this patent is extended or adjusted under 35 U.S.C. 154(b) by 276 days.

(21) Appl. No.: 16/614,596

(22) PCT Filed: May 10, 2018

(86) PCT No.: PCT/CN2018/086249
§ 371 (c)(1),
(2) Date: Nov. 18, 2019

(87) PCT Pub. No.: WO2018/210175
PCT Pub. Date: Nov. 22, 2018

(65) Prior Publication Data
US 2020/0082527 A1 Mar. 12, 2020

(30) Foreign Application Priority Data
May 19, 2017 (CN) .......................... 201710358487.4

(51) Int. Cl.
*G06K 9/00* (2022.01)
*B41M 5/00* (2006.01)
(Continued)

(52) U.S. Cl.
CPC .............. *G06T 7/0012* (2013.01); *A61B 6/06* (2013.01); *A61B 6/08* (2013.01); *A61B 6/469* (2013.01);
(Continued)

(58) Field of Classification Search
USPC ........ 382/100, 103, 106–107, 128–132, 168, 382/173, 181, 199, 254, 286–291, 305,
(Continued)

(56) References Cited

U.S. PATENT DOCUMENTS 9,700,209 B2   7/2017 Florent et al.
9,724,061 B2   8/2017 Hyung et al.
(Continued)

FOREIGN PATENT DOCUMENTS

CN   103429158 A   12/2013
CN   104602608 A    5/2015
(Continued)

OTHER PUBLICATIONS

International Search Report attached to International application dated Aug. 1, 2018, for International Application No. PCT/CN2018/086249.

(Continued)

*Primary Examiner* — Seyed H Azarian
(74) *Attorney, Agent, or Firm* — Banner & Witcoff Ltd.

(57) ABSTRACT

The present disclosure provides an X-ray exposure area regulation method, a storage medium, and an X-ray system. The X-ray exposure area regulation method may include: monitoring the state of an object under test (OUT) in real time and acquiring an initial image of the OUT when the state of the OUT satisfies the preset condition, determining an area of interest (AOI) in said initial image, and setting said X-ray exposure area based on the information of said AOI. Automatic regulation of an exposure area in the X-ray system can be realized according to the OUT. This not only facilitates operations and improves test efficiency, but also frees patients from exposure to unnecessary radiations.

16 Claims, 5 Drawing Sheets

(51) Int. Cl.
*G06T 7/00* (2017.01)
*G06T 7/11* (2017.01)
*A61B 6/06* (2006.01)
*A61B 6/08* (2006.01)
*A61B 6/00* (2006.01)

(52) U.S. Cl.
CPC ............ *A61B 6/5211* (2013.01); *A61B 6/542* (2013.01); *G06T 7/11* (2017.01); *G06T 2207/10116* (2013.01); *G06T 2207/20104* (2013.01)

(58) Field of Classification Search
USPC .............................. 382/321; 378/5, 8, 21, 28
See application file for complete search history.

(56) References Cited

U.S. PATENT DOCUMENTS

| | | | |
|---|---|---|---|
| 9,904,998 B2* | 2/2018 | Jockel | ...................... A61B 6/08 |
| 9,997,269 B2 | 6/2018 | Roh et al. | |
| 2007/0011635 A1 | 5/2007 | Dewaele | |
| 2008/0144764 A1* | 6/2008 | Nishide | .................. A61B 6/542 |
| | | | 378/5 |
| 2011/0222647 A1* | 9/2011 | Sugita | .................. G01N 23/046 |
| | | | 378/8 |
| 2015/0013938 A1 | 5/2015 | Hyung et al. | |
| 2016/0135767 A1 | 5/2016 | Kim | |
| 2016/0287192 A1* | 10/2016 | Cai | .......................... A61B 6/06 |
| 2020/0093450 A1* | 3/2020 | Melman | ............... A61B 6/5205 |

FOREIGN PATENT DOCUMENTS

| | | |
|---|---|---|
| CN | 104644197 A | 5/2015 |
| CN | 104783820 A | 7/2015 |
| CN | 106264589 A | 1/2017 |
| WO | 2016063234 A1 | 4/2016 |
| WO | 2016200370 A1 | 12/2016 |

OTHER PUBLICATIONS

Chinese Action dated Apr. 2, 2021, Application No. 201710358487.4.

* cited by examiner

X-RAY EXPOSURE AREA REGULATION METHOD, A STORAGE MEDIUM, AND AN X-RAY SYSTEM

CROSS-REFERENCE TO RELATED APPLICATIONS

The present application is a national stage entry of PCT application no. PCT/CN2018/086249, filed on May 10, 2018, which claims the benefit of the filing date of China patent application no. 201710358487.4, filed on May 19, 2017, the contents of which are incorporated herein by reference in their entirety.

TECHNICAL FIELD

The present disclosure relates to the technical field of medical devices, and in particular relates to an X-ray exposure area regulation method in an X-ray system, a storage medium, and an X-ray system.

BACKGROUND ART

Medical X-ray devices can be used for X-ray irradiation on a patient to obtain an X-ray image of the patient. When X-ray imaging equipment is used, proper X-ray irradiation ranges need to be regulated according to the conditions of different patients and the imaging requirements. Usually, an irradiation range is preset for a medical device in a mode. However, a default irradiation range is not always proper because of individual differences of patients. Therefore, the operator needs to manually regulate the medical device until the irradiation range is proper.

The above-mentioned way of manually regulating the exposure area has many shortcomings. It not only increases the operation burden of the operator, but also lowers the overall efficiency. In addition, when an X-ray exposure area is improperly selected, a patient will be subjected to unnecessary radiations and the quality of the image will also directly be affected.

CN203576524U relates to an X-ray camera device and an assisted positioning system. The X-ray camera device comprises a first display, a second display, and a camera. Said first display is used to display a standard position for a patient, said camera is used to acquire the position image of said patient and transfer the acquired position image to said second display, and said second display is used to display the overlapped image of said position image of said patient with an automatic exposure control area and a beam combiner opening area of a beam combiner.

SUMMARY OF THE DISCLOSURE

In view of this, an X-ray exposure area regulation method in an X-ray system is provided in one aspect of the present disclosure, a storage medium is provided in another aspect, and an X-ray system is provided in a further aspect.

According to one embodiment of the present disclosure, the X-ray exposure area regulation method comprises: monitoring the state of an OUT in real time and acquiring an initial image of the OUT when the state of the OUT satisfies the preset condition, determining an area of interest (AO') in said initial image, and setting said X-ray exposure area based on the information of said AOI.

The X-ray exposure area regulation method can further comprise: preprocessing said initial image to form a preprocessed image, segmenting said preprocessed image to form a plurality of segmented areas, and selecting an AOI in said plurality of segmented areas.

Said preprocessing can comprise binarization processing and contour processing.

Said preprocessed image is segmented by use of the watershed algorithm to obtain a distance map, and said plurality of segmented areas are formed on said distance map.

The X-ray exposure area regulation method can further comprise: selecting said AOI according to the distance between the central point of said plurality of segmented areas and the projection point of the center of the field of view of X-rays on said distance map.

The X-ray exposure area regulation method can further comprise: identifying the contour of said OUT in said preprocessed image, forming a bounding polygon for the contour of said OUT to obtain a polygon connected area, and determining the information about said AOI based on said polygon connected area.

The information about said AOI can include size information about said AOI, and setting said X-ray exposure area based on the information about said AOI comprises setting said X-ray exposure area according to preset redundant information based on the size information about said AOI.

Said initial image can be a thermal image or an optical image.

According to one embodiment, program instructions are stored in a computer storage medium (e.g. a non-transitory computer-readable medium) and said program instructions are executed to realize any above-mentioned method.

According to one embodiment, the X-ray system comprises a collimator, a camera used to monitor the state of an OUT in real time and acquire an initial image of said OUT when the state of said OUT satisfies a preset condition, and a control component. Said control component is connected to said collimator and said camera in a communication mode and is used to determine an AOI in said initial image and set an X-ray exposure area based on the information about the AOI.

Said control component can further be configured to preprocess said initial image to form a preprocessed image, segment said preprocessed image to form a plurality of segmented areas, and select an AOI in said plurality of segmented areas.

Said preprocessing can comprise binarization processing and contour processing. Said control component can further be configured to segment said preprocessed image by use of the watershed algorithm to obtain a distance map and form said plurality of segmented areas on said distance map. Said control component can further be configured to select said AOI according to the distance between the central point of said plurality of segmented areas and the projection point of the center of the field of view of X-rays on said distance map. Said control component can further be configured to identify the contour of said OUT in said preprocessed image, form a bounding polygon for the contour of said OUT to obtain a polygon connected area, and determine the information about said AOI based on said polygon connected area.

Said control component can further be configured to regulate said polygon connected area based on the angle of inclination or deflection of said collimator.

The information about said AOI can include size information about said AOI.

Said control component can further be used to set said X-ray exposure area according to preset redundant information based on the size information about said AOI.

Said camera can be an infrared imaging camera or an optical imaging camera, or said X-ray system can comprise an infrared imaging camera and an optical imaging camera.

According to one embodiment, the X-ray system comprises a collimator, a camera used to monitor the state of an OUT in real time and acquire an initial image of said OUT when the state of said OUT satisfies the preset condition, a control component connected to said camera in communication mode and used to determine an AOI in said initial image, and a console connected in communication mode to said control component which is used to receive the information about said AOI from said console and set an X-ray exposure area based on the information about the AOI.

In the present disclosure, an ordinary 2D camera (for example, visible light camera or thermal camera) can be used to realize automatic regulation of an exposure area in the X-ray system according to an OUT (for example, a body part of a patient). With the image quality guaranteed, the present disclosure can not only facilitate operations and improve test efficiency, but also free the patient from exposure to unnecessary radiations.

BRIEF DESCRIPTION OF THE DRAWINGS

The following will describe in detail the embodiments of the present disclosure by reference to the drawings so that those skilled in the art can have a clearer idea of the above-mentioned and other characteristics and advantages of the present disclosure.

DESCRIPTION OF REFERENCE NUMBERS IN THE DRAWINGS

| | |
|---|---|
| 100 | X-ray exposure area regulation method |
| S110-S130 | Steps |
| 1, 2, 10, 20 | Polygon connected area |
| 400, 500 | X-ray system |
| 410, 510 | Collimator |
| 420, 520 | Camera |
| 430, 530 | Control component |
| 540 | Console |

DETAILED DESCRIPTION OF THE DISCLOSURE

To aid understanding of the technical characteristics, objectives, and effect of the present disclosure more clearly, the following describes the specific embodiments of the present disclosure by reference to the drawings in which the same reference number represents the same component.

In this document, "schematic" means "acting as an instance, example, or illustration", and any schematic illustration or embodiment described in this document should not be interpreted as a more preferred or advantageous technical solution.

For the sake of simplicity of the drawings, only the parts related to the present disclosure are shown for a schematic purpose and they do not represent actual structures of a product. In addition, only one of the components which have the same structure or function is depicted or marked for a schematic purpose in some drawings so that the drawings are simplified to aid understanding.

In this document, "one" not only represents "only one", but also may represent "more than one". In this document, "first" and "second" are used only to distinguish from each other, but do not represent their importance or sequence, or a prerequisite for their mutual existence.

The "X-ray system" appearing in this document includes different types of X-ray imaging devices applied in the medical field. The "OUT" refers to an object to be tested by use of the X-ray system and it can be a part or parts of the body of a patient. In the images/surveillance videos formed by use of a camera, the "OUT" often includes not only the object to be tested, but also other parts of the body. For example, when a foot of the patient is going to be tested, the ankle and the lower leg may be included in the images/surveillance videos. The "OUT" should be interpreted as the body parts obtained in images/surveillance videos, including foot, ankle, and lower leg, for example, but should not be limited to only the object to be tested (for example, foot). In practice, the operator (for example, medical staff) can use the human-machine interface (for example, display device, keyboard, and mouse located on one side of the console of the X-ray system) to select the specific part to be tested, that is to say, select or set the content of the AOI from the images in the camera in advance.

Figure 1:
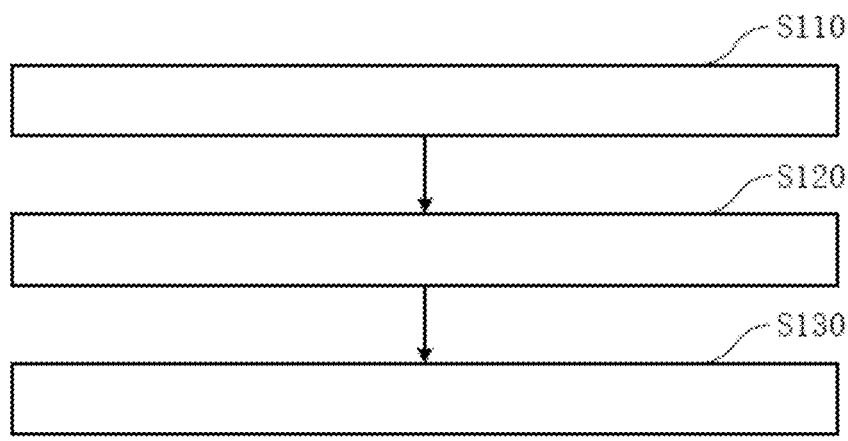
FIG. 1 is a schematic flow chart of the X-ray exposure area regulation method in one embodiment of the present disclosure.

First, see FIG. 1. FIG. 1 is a schematic flow chart of the X-ray exposure area regulation method in one embodiment of the present disclosure. In the embodiment shown in FIG. 1, the X-ray exposure area regulation method (100) can comprise the following steps:

Step S110: monitor an OUT in real time and acquire an initial image of the OUT, Step S120: determine an AOI in the initial image, and Step S130: set the X-ray exposure area based on the information of the AOI.

To be specific, the state of an OUT is monitored in real time and an initial image of the OUT is acquired when the state of the OUT satisfies the preset condition (Step S110). The OUT in the exemplary illustration is a hand of a patient. During the process in which the patient places the hand on the test platform (for example, the surface of the detector of the X-ray system) after entering the examination room, the change process of the hand of the patient from gross movement to fine movement and a standstill is monitored in real time. When finding from the surveillance equipment that the movement of the hand becomes slow and the state satisfies the preset condition, images are collected for the hand in photographing mode. The preset condition can be a threshold set for the time frequency or position movement amplitude of the position change of the OUT, and thus it can be used to determine whether the movement of the OUT becomes slow or stops (becomes standstill). In practice, those skilled in the art can set different preset conditions and the corresponding thresholds according to the practical application requirements, and the present disclosure is not restricted in this aspect.

An AOI in the initial image is determined (Step S120). For example, the area where the OUT (for example, the hand of the patient) is located in the image is found. Next, the X-ray exposure area is set based on the information of the AOI (Step S130). Thus, the X-ray exposure area of the X-ray system can adapt to the OUT.

The initial image can be a thermal image or an optical image. The following describes in detail the schematic X-ray exposure area regulation methods in combination with FIG. 2A to FIG. 2D, and FIG. 3A to FIG. 3E, respectively. FIG. 2A to FIG. 2D show the images obtained in the steps of an initial image process which is a thermal image, and FIG. 3A to FIG. 3E show the images obtained in the steps of an initial image process which is an optical image.

In the embodiments, the X-ray exposure area regulation method in the X-ray system can further comprise the following steps: preprocessing the initial image to form a preprocessed image, segmenting said preprocessed image to form a plurality of segmented areas, and selecting an AOI in the plurality of segmented areas.

To be specific, preprocessing can comprise binarization processing and contour processing to determine the contour of the OUT. In other variant embodiments, those skilled in the art can easily think of other preprocessing methods, not limited to the above-illustrated content, for the initial image.

Figure 2A:
FIG. 2A to FIG. 2D show the images obtained in the steps of an initial image which is a thermal image.
Figure 2B:
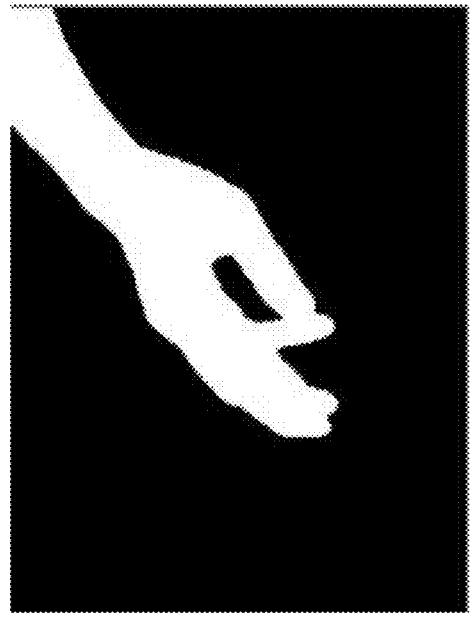
Figure 2C:
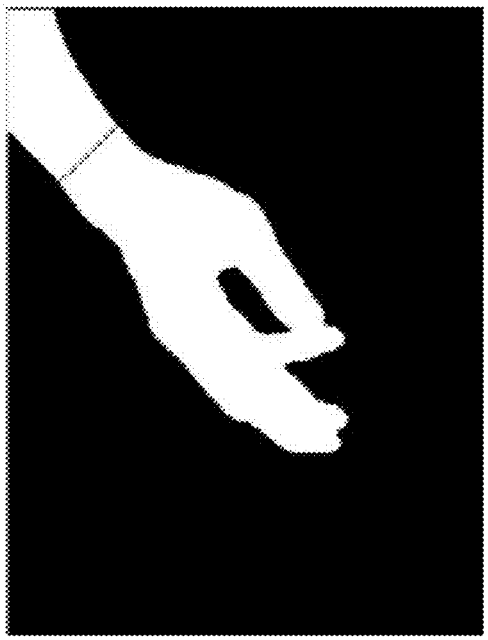
Figure 2D:
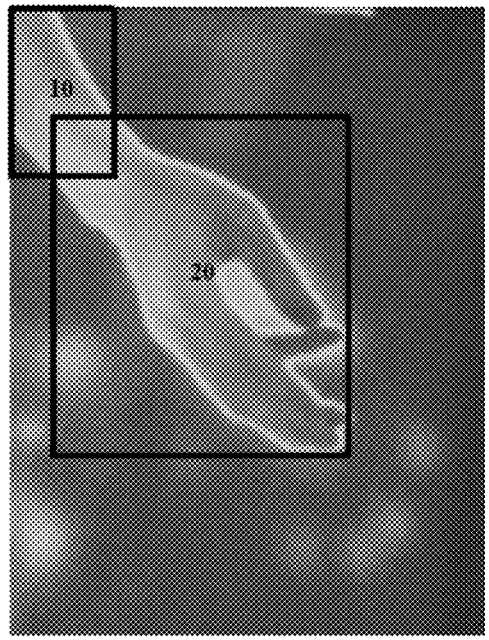

FIG. 2A shows an initial image (thermal image), FIG. 2B shows the preprocessed image obtained after binarization processing for the initial image, FIG. 2C shows image segmentation of the preprocessed image, and FIG. 2D shows the formation of the polygon connected area in the image. As shown in FIG. 2C and FIG. 2D, the preprocessed image is segmented to form a plurality of segmented areas and an AOI is selected from the plurality of segmented areas. Two segmented areas are shown for schematic description. In practice, an initial image can be segmented into more areas according to different OUTs and the obtained initial image.

In the embodiment shown in FIG. 2A to FIG. 2D, the OUT is a hand of a patient, and the initial image includes not only the hand of the patient, but also the arm of the patient. From experience, the thinnest part between the hand and the arm is usually the wrist and hence the boundary between the hand and the arm can be determined. The area where the hand is located is selected as an AOI in the image, and the X-ray exposure area in the X-ray system is regulated according to the AOI. Optionally, the watershed algorithm is used to segment the preprocessed image to obtain a distance map, form a plurality of segmented areas on the distance map, and select an AOI from the plurality of segmented areas. The AOI is selected according to the distance between the central point of the plurality of segmented areas and the projection point of the center of the field of view of X-rays on the distance map. For example, a segmented area is selected whose central point is closer to the projection point than the AOI. In practice, the projection point of the center of the field of view of X-rays on the distance map can overlap the center of the whole image, or may not overlap the center of the whole image for the reason of shift.

In the embodiments of the present disclosure, the X-ray exposure area regulation method in the X-ray system can further comprise the following steps: identifying the contour of the OUT in the preprocessed image, forming a bounding polygon for the contour of the OUT to obtain the polygon connected area, and determining the information about the AOI is determined based on said polygon connected area.

The above-mentioned process is described in combination with FIG. 2D. The contours of the hand and the arm are identified in the preprocessed image, bounding polygons are formed respectively based on the contours of the hand and the arm, the polygon connected areas are obtained, and the information about the AOI is determined based on the polygon connected area containing the hand. For the sake of clarity, the connected areas of the polygons are shown in the initial image in FIG. 2A to form FIG. 2D. As shown in FIG. 2D, the polygon connected area (10) and the polygon connected area (20) are connected areas of the arm and the hand, respectively. A polygon connected area of interest is selected from a plurality of polygon connected areas and the information about the AOI is determined. In practice, a polygon connected area of interest can automatically be selected from a plurality of polygon connected areas as an AOI according to the specific part which the operator selects in advance to test, or the operator can select a polygon connected area of interest on the human-machine interface. When the initial image contains a plurality of body parts and more than one part is an OUT, a plurality of connected areas can be determined to be AOIs.

In a variant embodiment, a bounding polygon can be formed only based on the contour of the hand to obtain a polygon connected area, and the polygon connected area will be used as an AOI to determine the information about the AOI. In other words, in this case, there is only one polygon connected area (20) in FIG. 2D.

In the above-mentioned embodiments, the information about the AOI can include size information about the AOI. Thus, the X-ray exposure area can be set according to the size scale of the AOI to the X-ray exposure area and the preset redundant information based on the information about the AOI. For example, in practice, the X-ray exposure area is slightly larger than the AOI.

Figure 3A:
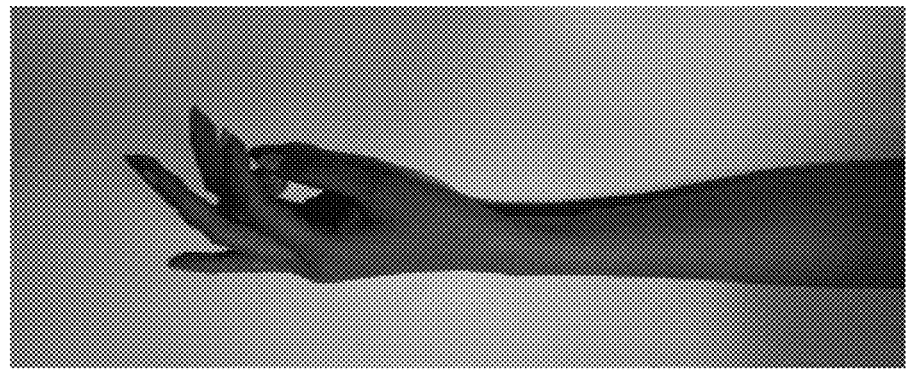
FIG. 3A to FIG. 3E show the images obtained in the steps of an initial image which is an optical image.
Figure 3B:
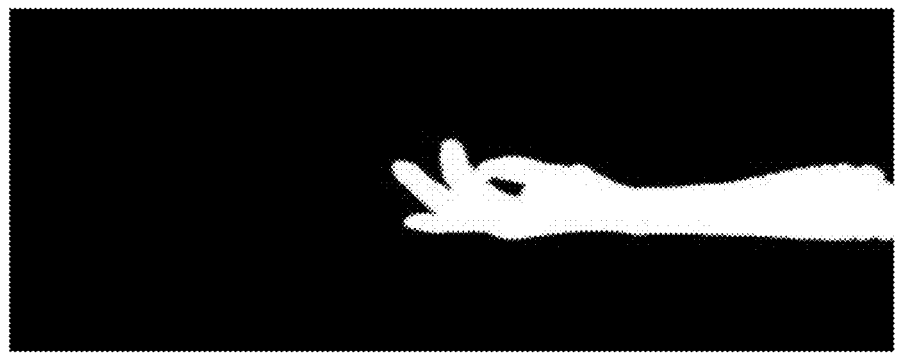
Figure 3C:
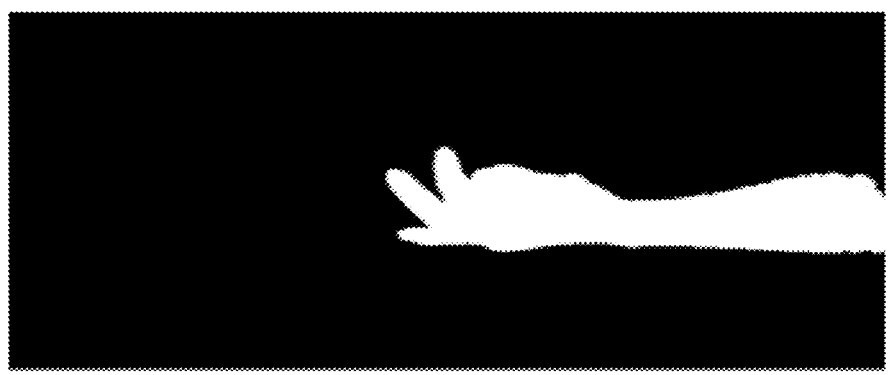
Figure 3D:
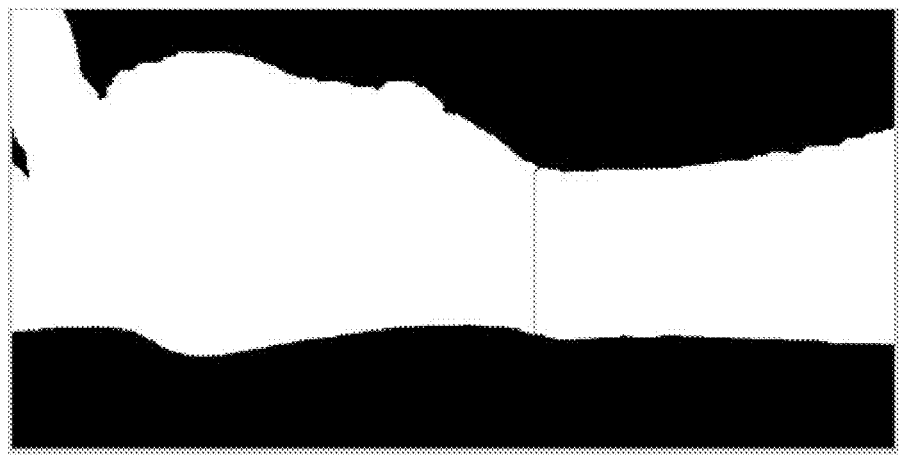
Figure 3E:
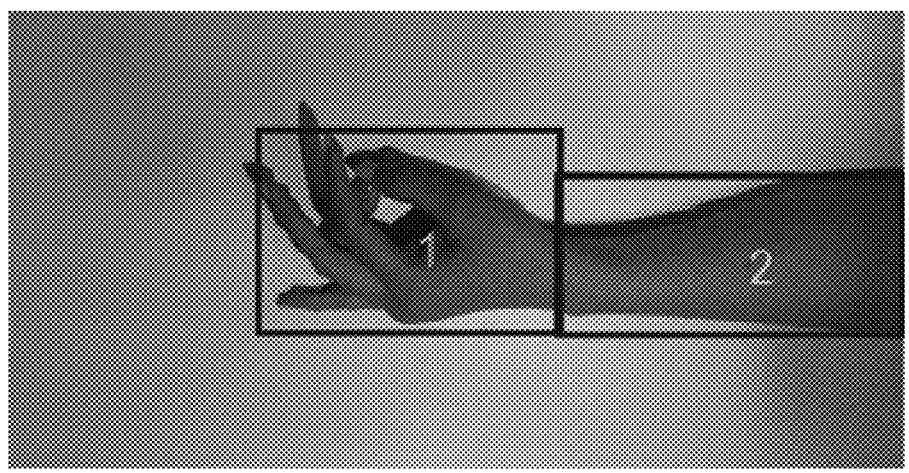

FIG. 3A to FIG. 3E show the images obtained in the steps of an initial image process, which is an optical image. FIG. 3A shows an initial image (optical image), FIG. 3B shows a preprocessed image obtained after binarization processing for the initial image. FIG. 3D shows image segmentation of the preprocessed image, and FIG. 3E shows the formation of the polygon connected area in the image.

The processing of an optical image is similar to the previously-described processing of a thermal image. In a variant embodiment, the preprocessed image obtained after binarization processing can further be processed. As shown in FIG. 3C, "loophole filling" processing can be performed for the preprocessed image. Loophole filling can be adopted during the previously-described processing of a thermal image, but is not limited to the processing of an optical image. "Loophole filling" processing is a conventional image processing means and is not the key point which needs to be improved in the present disclosure. Therefore, the loophole filling processing is not detailed here.

In other embodiments, the X-ray exposure area regulation method can further comprise other steps, for example, optimization or noise reduction/interference information elimination, and other preprocessing steps, so as to optimize the image quality. The present disclosure is not restricted in this aspect.

The following will describe the X-ray system of the present disclosure in combination with the drawings.

Figure 4:
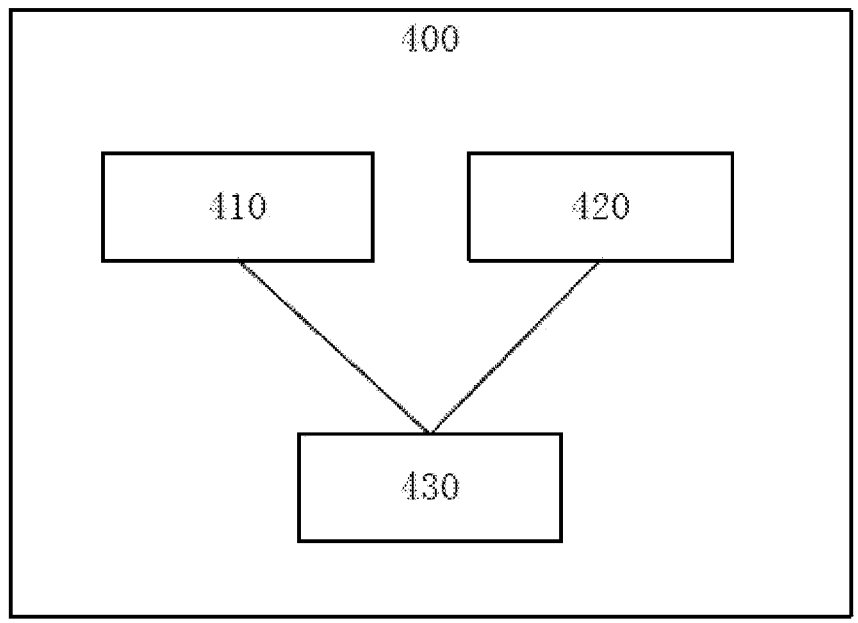
FIG. 4 is a schematic block diagram for the X-ray system in one embodiment of the present disclosure.

FIG. 4 is a schematic block diagram for the X-ray system in one embodiment of the present disclosure. In the embodiment shown in FIG. 4, the X-ray system (400) comprises a collimator (410), a camera (420), and a control component (430). The camera (420) is used to monitor the state of an OUT in real time and acquire an initial image of the OUT when the state of the OUT satisfies the preset conditions. The control component (430) is connected to the collimator (410) and the camera (420) in communication mode and is used to determine an AOI in the initial image and set an X-ray exposure area based on the information about the AOI.

In the embodiment, the camera (420) can be an infrared imaging camera or an optical imaging camera, or the X-ray system (400) can comprise an infrared imaging camera and an optical imaging camera. The camera (420) can be set on a lateral side of the collimator (410) or on a side where the collimator (410) is opposite to the detector of the X-ray system. Those skilled in the art can place one or more cameras (420) in proper positions according to the actual requirements. In other words, the quantity, types, and positions of the cameras which are set and utilized in the present disclosure are not restricted.

In the X-ray system of the present disclosure, the control component (430) can be a console which controls the overall function of the X-ray system. According to the actual conditions, an alternative control device can be set to realize the function of the control component (430). The control device can be set in the console, or can be configured to be independent of the console. The present disclosure is not restricted in this aspect.

Figure 5:
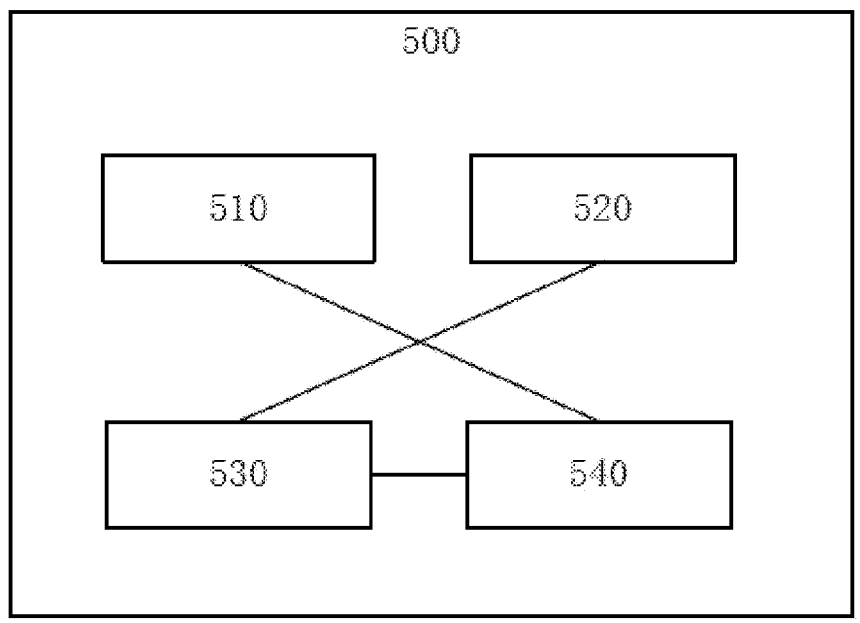
FIG. 5 is a schematic block diagram for the X-ray system in another embodiment of the present disclosure.

FIG. 5 is a schematic block diagram for the X-ray system configured with an independent control device. The X-ray system (500) comprises a collimator (510), a camera (520), a control component (530), and a console (540). The camera (520) is used to monitor the state of an OUT in real time and acquire an initial image of the OUT when the state of the OUT satisfies the preset conditions. The control component (530) is connected to the camera (520) in communication mode and is used to determine an AOI in an initial image. The console (540) is connected in communication mode to the control component (530), which is used to receive the information about the AOI from the console (540) and set an X-ray exposure area based on the information about the AOI.

In the embodiments, the control component (430 or 530) can further be configured to preprocess an initial image to form a preprocessed image, segment the preprocessed image to form a plurality of segmented areas, and select an AOI in the plurality of segmented areas. In practice, preprocessing can comprise binarization processing and contour processing so as to determine the contour of an OUT.

In the embodiments, the control component (430 or 530) can further be configured to segment the preprocessed image by use of the watershed algorithm to obtain a distance map, form a plurality of segmented areas on the distance map, and select a segmented area of interest from said plurality of segmented areas. Further, the control component (430 or 530) can be configured to select an AOI according to the distance between the central point of the plurality of segmented areas and the projection point of the center of the field of view of X-rays on the distance map. For example, a segmented area is selected whose central point is closer to the projection point than the AOI. In practice, the projection point of the center of the field of view of X-rays on the distance map can overlap the center of the whole image, or may not overlap the center of the whole image for the reason of shift.

In the embodiments, the control component (430 or 530) can further be configured to identify the contour of the OUT in the preprocessed image, form a bounding polygon for the contour of the OUT to obtain the polygon connected area, and determine the information about said AOI based on said polygon connected area.

In the embodiments, the control component (430 or 530) can further be configured to regulate the polygon connected area based on the angle of the collimator (410 or 510). In other words, when the collimator (410 or 510) is slightly inclined or deflected relative to the detector of the X-ray system, the polygon connected area on the image can be inclined or deflected accordingly based on the angle of inclination or deflection of the collimator (410 or 510). In this way, in the embodiment shown in FIG. 2D or FIG. 3E, the rectangle connected area can be inclined or deflected on the image.

In the embodiments, the information about an AOI can include size information about the AOI, and the control component (430 or 530) can further be used to set an X-ray exposure area according to preset redundant information based on the size information about the AOI.

The present disclosure further provides a computer storage medium, which may be implemented as a non-transitory computer-readable medium. Program instructions are stored in said computer storage medium and said program instructions can be executed to realize any of the methods described herein. To be specific, a system or device equipped with a storage medium can be provided. Software program codes, which can realize the function in any of above-mentioned embodiments, are stored in the storage medium and the computer (or CPU or MPU) of the system or device can read and execute the program codes stored in the storage medium.

In this case, program codes read from the storage medium themselves can realize the function in any of the above-mentioned embodiments. Therefore, program codes and the storage medium where program codes are stored constitute a part of the present disclosure.

Embodiments of storage media used to provide program codes include any suitable forms such as, for instance, floppy disk, hard disk, magneto-optical disk, compact disk (for example, compact disk read-only memory (CD-ROM)), compact disk—recordable (CD-R), compact disk—rewritable (CD-RW), digital versatile disk—read only memory (DVD-ROM), digital versatile disk—random access memory (DVD-RAM), digital versatile disk±rewritable (DVD±RW), magnetic tape, non-volatile memory card, and read-only memory (ROM). Optionally, program codes can be downloaded from a server computer over a communication network.

In addition, it should clearly be understood that the function of any of the above-mentioned embodiments can be realized not only by executing the program codes read out by a computer, but also by the operating system running on the computer completing a part or all of its practical operations through a program code-based instruction.

In addition, it should be understood that the program codes read out from a storage medium are written into the storage in the expansion board in a computer or are written into a storage in an expansion unit connected to the computer, and then the instruction based on program codes enables the CPU installed on the expansion board or expansion unit to execute a part or all of its practical operations to realize the function of any of the above-mentioned embodiments.

In summary, the present disclosure provides an X-ray exposure area regulation method, a storage medium, and an X-ray system. According to one embodiment of the present disclosure, the X-ray exposure area regulation method comprises: monitoring the state of an OUT in real time and acquiring an initial image of the OUT when the state of the OUT satisfies the preset conditions, determining an AOI in said initial image, and setting said X-ray exposure area based on the information of said AOI. In the present disclosure, an ordinary 2D camera (for example, visible light camera or thermal camera) can be used to realize automatic regulation of an exposure area in the X-ray system according to an OUT (for example, a body part of a patient). With the image quality guaranteed, the present disclosure can not only facilitate operations and improve test efficiency, but also free the patient from exposure to unnecessary radiations.

The above-mentioned embodiments are preferred embodiments of the present disclosure, but are not used to restrict the present disclosure. Without departing from the spirit and principle of the present disclosure, modifications, equivalent replacements, and improvements should all fall within the scope of protection of the present disclosure.

The invention claimed is:

1. An X-ray exposure area regulation method, the method comprising:
   monitoring a state of an object under test (OUT) in real time;
   acquiring an initial image of the OUT when the state of the OUT satisfies a predetermined condition;
   preprocessing the initial image of the OUT to form a preprocessed image;
   segmenting the preprocessed image to form a plurality of segmented areas;
   segmenting, via a watershed algorithm, the preprocessed image to obtain a distance map;
   forming the plurality of segmented areas on the distance map;
   selecting an area of interest (AOI) from within the plurality of segmented areas to determine the AOI in the initial image; and
   setting an X-ray exposure area based on information associated with the determined AOI in the initial image.

2. The X-ray exposure area regulation method as claimed in claim 1, wherein the act of preprocessing includes one or more of binarization processing and contour processing.

3. The X-ray exposure area regulation method as claimed in claim 1, further comprising:
   selecting the AOI in an area between (i) a central point of the plurality of segmented areas, and (ii) a projection point of the center of a field of view of X-rays on the distance map.

4. The X-ray exposure area regulation method as claimed in claim 1, further comprising:
   identifying the contour of the OUT in the preprocessed image;
   forming a bounding polygon for the contour of the OUT to obtain a polygon-connected area; and
   determining the information about the AOI based on the polygon-connected area.

5. The X-ray exposure area regulation method as claimed in claim 1, wherein the information about the AOI includes size information about the AOI, and
   wherein the act of setting the X-ray exposure area includes setting the X-ray exposure area using predetermined redundant information based on the size information about the AOI.

6. The X-ray exposure area regulation method as claimed in claim 1, wherein the initial image is at least one of a thermal image or an optical image.

7. A non-transitory computer-readable storage medium having instructions stored thereon that, when executed by one or more processors, cause the one or more processors to:
   monitor a state of an object under test (OUT) in real time;
   acquire an initial image of the OUT when the state of the OUT satisfies a predetermined condition;
   preprocess the initial image of the OUT to form a preprocessed image;
   segment the preprocessed image to form a plurality of segmented areas;
   segment, via a watershed algorithm, the preprocessed image to obtain a distance map;
   form the plurality of segmented areas on the distance map;
   select an area of interest (AOI) from within the plurality of segmented areas to determine the AOI in the initial image; and
   set an X-ray exposure area based on information associated with the determined AOI in the initial image.

8. An X-ray system, comprising:
   a collimator;
   a camera configured to monitor a state of an object under test (OUT) in real time and to acquire an initial image of the OUT when a state of the OUT satisfies a predetermined condition; and
   a control component communicatively coupled to the camera, the control component being configured to:
      preprocess the initial image of the OUT to form a preprocessed image;
      segment the preprocessed image to form a plurality of segmented areas;
      segment, via a watershed algorithm, the preprocessed image to obtain a distance map;
      form the plurality of segmented areas on the distance map;
      select an area of interest (AOI) from within the plurality of segmented areas to determine the AOI in the initial image; and
      set an X-ray exposure area based on information associated with the determined AOI in the initial image.

9. The X-ray system as claimed in claim 8, wherein the preprocessing includes one or more of binarization processing and contour processing.

10. The X-ray system as claimed in claim 8, wherein the control component is further configured to select the AOI from an area between (i) a central point of the plurality of segmented areas, and (ii) a projection point of the center of a field of view of X-rays on the distance map.

11. The X-ray system as claimed in claim 8, wherein the control component is further configured to:
   identify a contour of the OUT in the preprocessed image;
   form a bounding polygon for the contour of the OUT to obtain a polygon-connected area; and
   determine the information about the AOI based on the polygon-connected area.

12. The X-ray system as claimed in claim 11, wherein the control component is further configured to incline or deflect the polygon-connected area based on an angle of inclination or deflection of the collimator.

13. The X-ray system as claimed in claim 8, wherein the information about the AOI includes size information about the AOI.

14. The X-ray system as claimed in claim 13, wherein the control component is further configured to set the X-ray exposure area using predetermined redundant information associated with the size information about the AOI.

15. The X-ray system as claimed in claim 8, wherein the camera comprises one of an infrared imaging camera or an optical imaging camera.

16. The X-ray system, as claimed in claim 8, further comprising:
   a console communicatively coupled to the control component, the control component being configured to receive the information about the AOI from the console.

* * * * *